(12) United States Patent
Aust et al.

(10) Patent No.: US 6,584,170 B2
(45) Date of Patent: Jun. 24, 2003

(54) METHOD AND APPARATUS FOR INSPECTING AN OBJECT, PARTICULARLY A PIECE OF LUGGAGE

(75) Inventors: Stefan Aust, Niedernhausen (DE); Cornelius Koch, Hochheim (DE); Claus Meder, Rossdorf (DE)

(73) Assignee: Heimann Systems GmbH, Wiesbaden (DE)

( * ) Notice: Subject to any disclaimer, the term of this patent is extended or adjusted under 35 U.S.C. 154(b) by 0 days.

(21) Appl. No.: 10/061,213

(22) Filed: Feb. 4, 2002

(65) Prior Publication Data

US 2003/0031293 A1 Feb. 13, 2003

(30) Foreign Application Priority Data

Aug. 11, 2001 (DE) .......................... 101 39 672

(51) Int. Cl.[7] ................................. H05G 1/64
(52) U.S. Cl. ........................................ 378/57
(58) Field of Search ........................ 378/57, 58

(56) References Cited

U.S. PATENT DOCUMENTS

| | | | | |
|---|---|---|---|---|
| 3,958,078 A | * | 5/1976 | Fowler et al. ................. | 378/57 |
| 5,400,381 A | * | 3/1995 | Steude et al. .................. | 378/57 |
| 5,600,303 A | * | 2/1997 | Husseiny et al. .............. | 378/57 |
| 5,692,029 A | | 11/1997 | Husseiny et al. | |
| 6,088,423 A | | 7/2000 | Krug et al. | |

FOREIGN PATENT DOCUMENTS

EP 0485872 5/1992

OTHER PUBLICATIONS

Abstract of European Patent No. EP 0 485 872 in the English language.

* cited by examiner

*Primary Examiner*—Craig E. Church
(74) *Attorney, Agent, or Firm*—Birch, Stewart, Kolasch & Birch, LLP

(57) ABSTRACT

In a device and processes for inspecting an object (1), particularly a piece of luggage, in which radiation is emitted by a stationary radiation source (2) while the object (1) is transported in a straight line through the radiation with intensity levels of unabsorbed radiation being detected by a detector arrangement (3) and processed into an image of the object (1), the object (1) is rotated by a rotating device (8) through an angle after a pass through the radiation in order to change its transport position, and is subsequently transported through the radiation again with another image being produced. This facilitates improved inspection by reducing so-called "dark alarms."

25 Claims, 8 Drawing Sheets

METHOD AND APPARATUS FOR INSPECTING AN OBJECT, PARTICULARLY A PIECE OF LUGGAGE

BACKGROUND OF THE INVENTION

This application claims a priority from German application 101 39 672.4, filed Aug. 11, 2001, and the contents of that application are incorporated herein by reference.

The invention relates to a method for inspecting an object, particularly a piece of luggage, in which radiation is emitted by a stationary radiation source while the object is transported in a straight line through the radiation and intensity levels of unabsorbed radiation are detected by a detector arrangement and processed into an image of the object, as well as to an apparatus for implementing such a method.

Processes and apparatus are known for inspecting objects, for example for security inspection of baggage at airports, wherein an object is transported in a straight line through radiation emitted by a stationary radiation source. The radiation not absorbed by the object is detected by a detector arrangement and processed into an image of the object, which is displayed on a screen for an operator. The inspection is typically performed using X-rays.

Since the unabsorbed radiation is detected in the inspection, a region in which the radiation is completely or almost completely absorbed is displayed on the image as a dark area. If it cannot be ruled out that another item, relevant from a security standpoint, is located behind the item that largely absorbs the radiation inside the object, a so-called "dark alarm" is triggered during the inspection. The object must then be subjected to an additional time-consuming security inspection; for example, suitcases are opened and examined manually.

An inspection system is disclosed in U.S. Pat. No. 6,088,423 that has three radiation sources that are arranged at different positions relative to a transport plane and emit radiation in three parallel planes. The radiation detected by three detector arrangements is processed by an analysis unit to determine probable outside contours of three-dimensional objects, one goal of which is to prevent false alarms.

An object of the invention is to provide a method and an apparatus for inspecting an object that permit improved inspection by reducing dark alarms with a low level of design complexity.

SUMMARY OF THE INVENTION

According to principles of this invention, with regard to the method, the object being inspected is rotated through an angle after a pass through radiation by a rotating device for changing its transport position and is subsequently transported through the radiation again with another image being produced. With regard to the apparatus, a transport device has the rotating device for rotating the object after the pass through the radiation to change its transport position.

According to the invention, only a single stationary radiation source is required. If the image generated by the first pass contains dark areas to be inspected, the object being inspected is rotated into a different transport position and an additional image is generated by the same radiation source. This process, controlled manually by an operator or automatically by a machine, can be repeated as many times as necessary until sufficient information has been obtained about the dark area in the first image.

In the simplest embodiment, an operator decides, based on the images available to him, whether and in what position the object is to be re-transported through the radiation and re-inspected. The analysis unit prepares the individual images of an object appropriately for this decision; preferably they are displayed next to each other or sequentially on a screen, and all facing in the same direction.

To provide as much support as possible to an operator for manual control of the inspection, current status parameters, or values, of the inspection process are displayed, in particular the angular position of the object and the number of passes that have been made through the radiation. Preferably the information is displayed on the screen of the analysis unit, although a separate display is also possible.

In a further enhanced embodiment, the process can be automated such that the discovery of a dark area triggers an automatic inspection routine. To this end, a computer automatically controls the number of passes and/or the angle of a pass as a function of parameters of the dark area. The particular angle of rotation and the chronological sequence of the display of the individual images of an object can be chosen such that the impression of a rotating object is produced on the screen. This type of display makes it easier for the operator viewing the image to decide whether the object should undergo another inspection stage or be examined manually as well.

In principle, rotation about all three spatial axes is possible in order to change the position of the object before another pass. Preferably, a direction of the rotational axis and a size of the angle are chosen such that the probability is greatest that no dark area will be produced on the next pass.

In the simplest embodiment, the object is rotated about only one axis. In this case, rotation about an axis perpendicular to the transport plane is preferred, since this can be accomplished with the least expense.

Preferably the object's direction of transport through the radiation is reversed each time, with an image generated at each pass through the radiation. Alternatively, it is also possible to produce images only during transport in a single direction. This simplifies analysis of the images for line-by-line detection, since they are all produced in the same direction relative to the radiation and thus can be displayed directly. To this end, either the object is not inspected when it is transported backward in a straight line past the radiation source, or the object is transported back for the next pass on a transport loop that leads outside and around the radiation source.

BRIEF DESCRIPTION OF THE DRAWINGS

The invention is described and explained in more detail with reference to the drawings. The described and drawn features can be used individually or in preferred combinations in other embodiments of the invention. The foregoing and other objects, features and advantages of the invention will be apparent from the following more particular description of the invention, as illustrated in the drawings in which reference characters refer to the same parts throughout the different views. The drawings are not necessarily to scale, emphasis instead being placed upon illustrating principles of the invention in a clear manner.

DETAILED DESCRIPTION OF THE INVENTION

Figure 1:
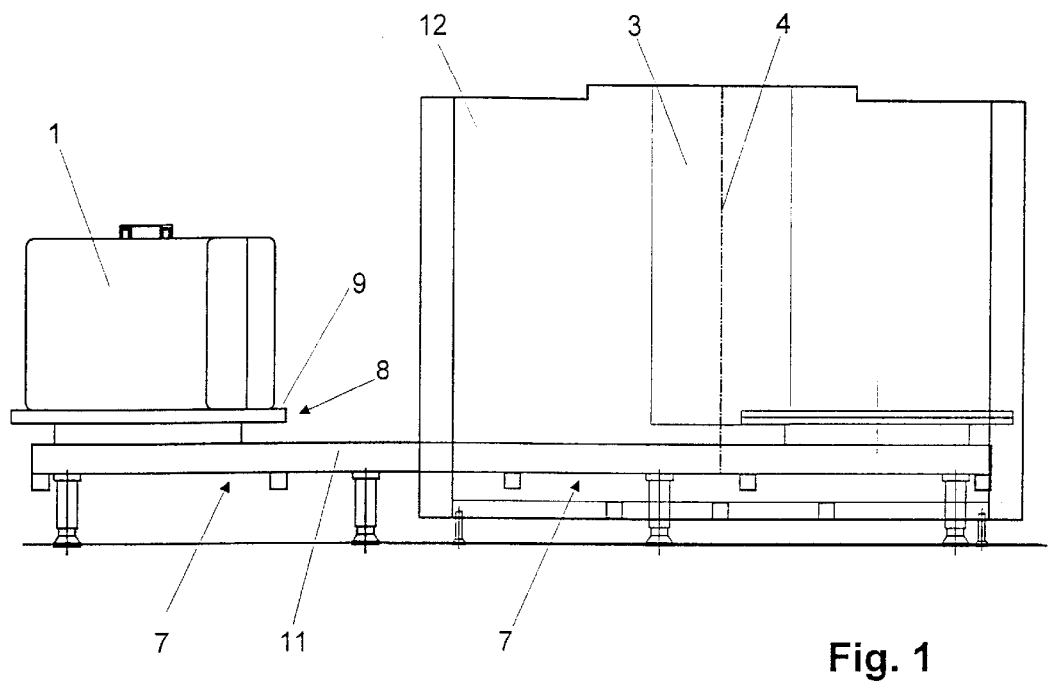
FIG. 1 is a side view of an inspection apparatus of the invention.

The inspection apparatus shown in the figures is used for security inspection of luggage 1, for example of suitcases, such as is performed at airports. The most important components of the apparatus are a fixed, or stationary, radiation source 2, preferably an X-ray source, and a detector arrangement 3 facing the radiation source 2. Preferably the radiation source 2 emits radiation in a fan-shaped radiation plane 4, and the detector arrangement 3 contains detectors in a linear arrangement. In the present embodiment, the radiation source 2 is arranged laterally next to and somewhat below objects 1 (pieces of luggage) to be inspected. The detector arrangement 3 facing the radiation source 2 is L-shaped so that all radiation passing through the object 1 is detected.

Furthermore, the apparatus has an analysis unit with a computer 5 and a screen 6. The computer generates an image from the intensity levels of the X-rays detected by the detector arrangement 3, and this image is displayed on the screen 6.

Figure 2:
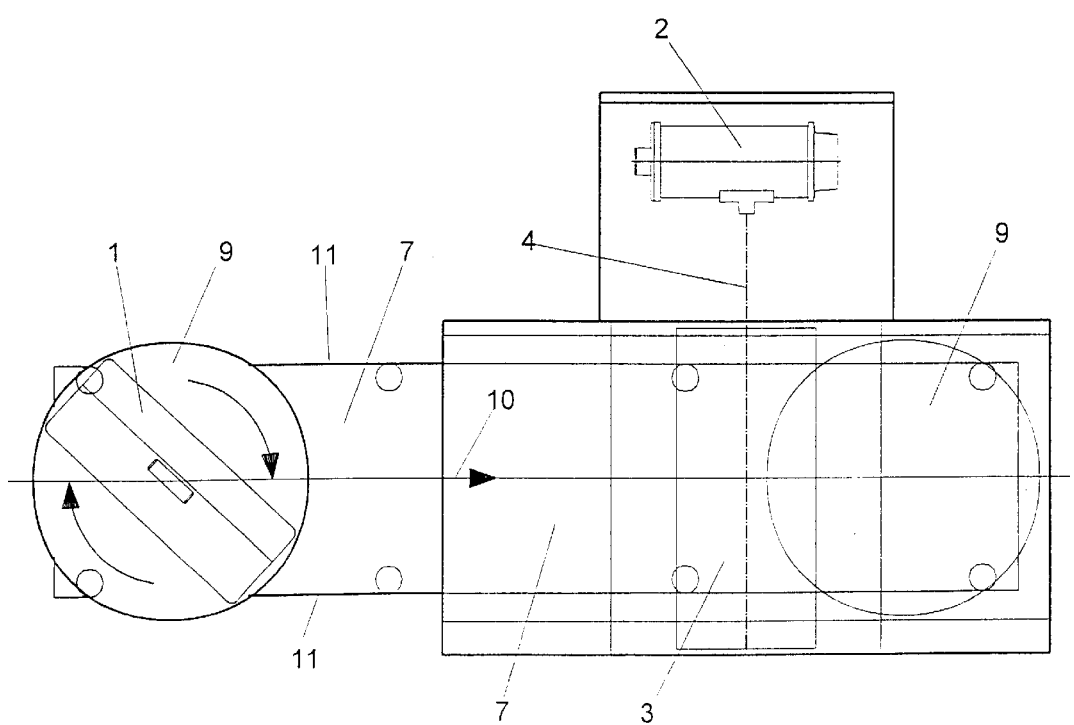
FIG. 2 is a top view of the apparatus of FIG. 1.

In order to transport the objects 1 to be inspected through the radiation—through the radiation plane 4 in the example—the inspection apparatus has a transport device 7 that conveys in a straight line. It is important to the invention that the transport devices 7 have a rotating device 8 that makes it possible to rotate the object 1 after a pass through the radiation (radiation plane 4) in order to change its transport position so that another image can be generated of the object 1 in a different transport position. Preferably the rotating device 8 has a transport plate 9 that is mounted such that it can be pivoted by a rotary actuator about an axis of rotation perpendicular to the transport plane, as shown in FIG. 2. Alternatively or in addition, the transport plate 9 is mounted such that it can be tilted by a tilt actuator about a tilt axis running in the direction of transport (arrow 10) or transverse to the direction of transport. Preferably the transport plate 9 with its rotary or tilt actuator is carried along a linear guide with two lateral guide rails 11, which are supported on a base and extend from a region in front of the radiation-shielded radiation tunnel 12 into the tunnel to a region beyond the radiation plane 4. Preferably the transport device 7 is reversible for transport in the opposite direction so that the object 1 can be transported through the radiation plane 4 in alternating directions. In the present embodiment, at every pass through the radiation plane 4, an image is generated that is displayed on the screen 6.

The computer 5 is also part of a control unit that controls the transport device 7 and the rotating device 8. For manual operation the computer 5, and hence the control unit, is connected to a control-panel unit, which in the shown embodiment is a keyboard 13, that an operator can use to specify the number of passes and the size of the angle of rotation. To provide as much support as possible to the operator for manual control of the inspection, display instruments are provided, with which the current status parameters, or values, of the inspection process are displayed, in particular the angular position of the object 1 and the number of passes that have been made through the radiation. Preferably the information is displayed on the screen 6 of the analysis unit. The images of an object 1 produced during the individual passes are displayed on the screen 6, either next to one another or in chronological sequence one after the other. In the shown embodiment, because images are also produced during transport in the reverse direction, the analysis unit processes the individual images in such a way that they all face the same direction when displayed on the screen 6. This makes it easier for the operator to decide whether an additional image should be made of the object in another transport position and if so, the angle of rotation by which the object 1 should be rotated.

In an enhanced design, the inspection apparatus includes a control unit with a computer that automatically controls the number of passes and/or the size of the angle of rotation before a pass. It is preferable for the number of images and the respective angles of rotation of the object 1 to be chosen such that the individual images can be sequenced in a fashion similar to a film. The analysis unit then displays the individual images of an object 1 in their chronological order on the screen 6 in such a way that the impression of a rotating object is produced on the screen.

A sequence of inspection of an object 1 is shown schematically in FIGS. 3 through 8.

Figure 3:
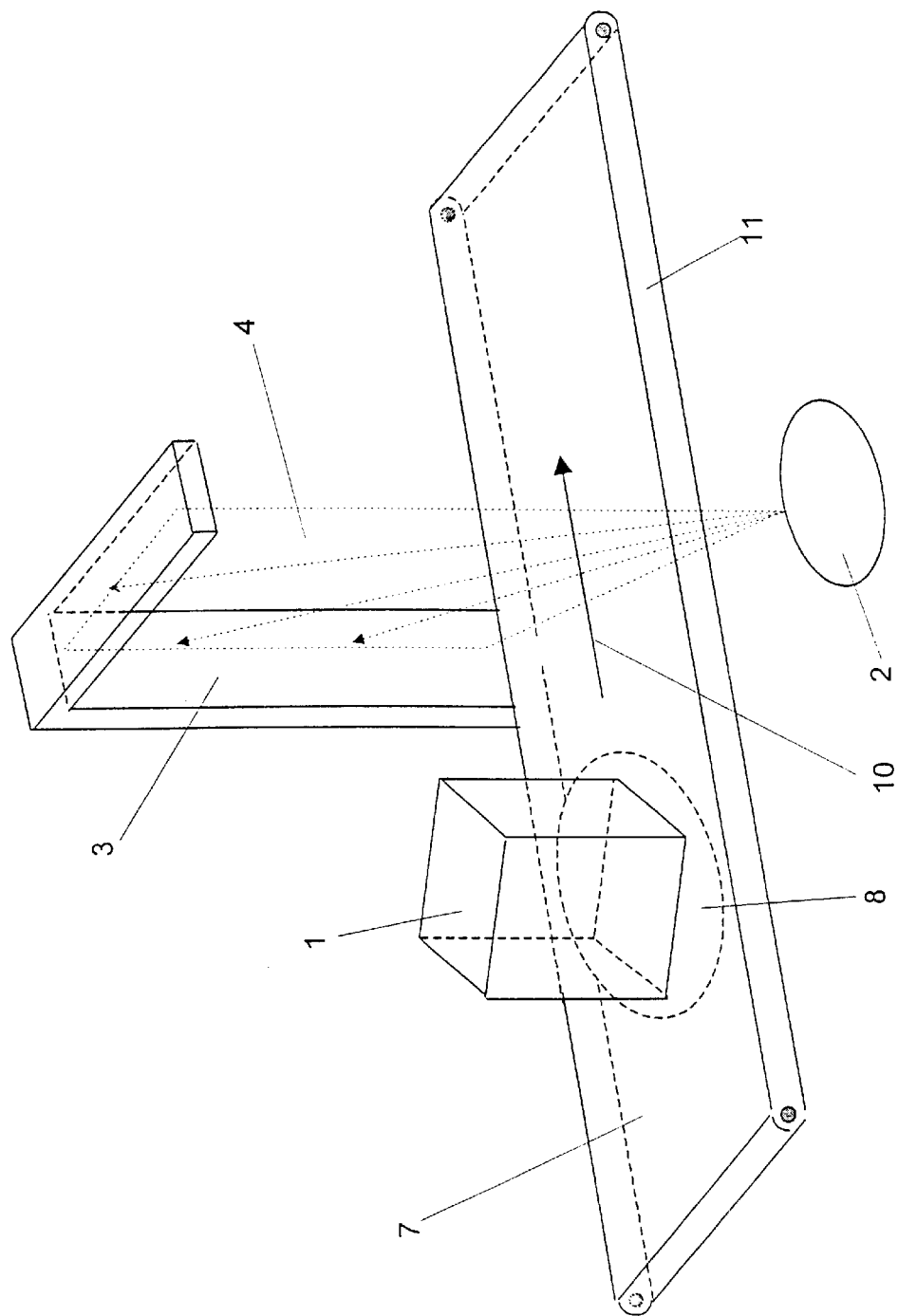
FIGS. 3–8 are isometric schematic representations of steps in a sequence of an inspection process of this invention.

The object 1 is placed on the transport plate 9 of the transport device 7, with the transport plate 9 being located in front of the radiation tunnel 12 (FIG. 3). Then the object 1 is conveyed in a straight line through the radiation, while the intensity levels of the unabsorbed radiation are detected by the detector arrangement 3 and processed into an image of the object 1. Preferably the radiation source 2 emits X-rays in the radiation plane 4, and the intensity of the unabsorbed radiation is detected by the detector arrangement 3 in line-by-line fashion.

Figure 4:
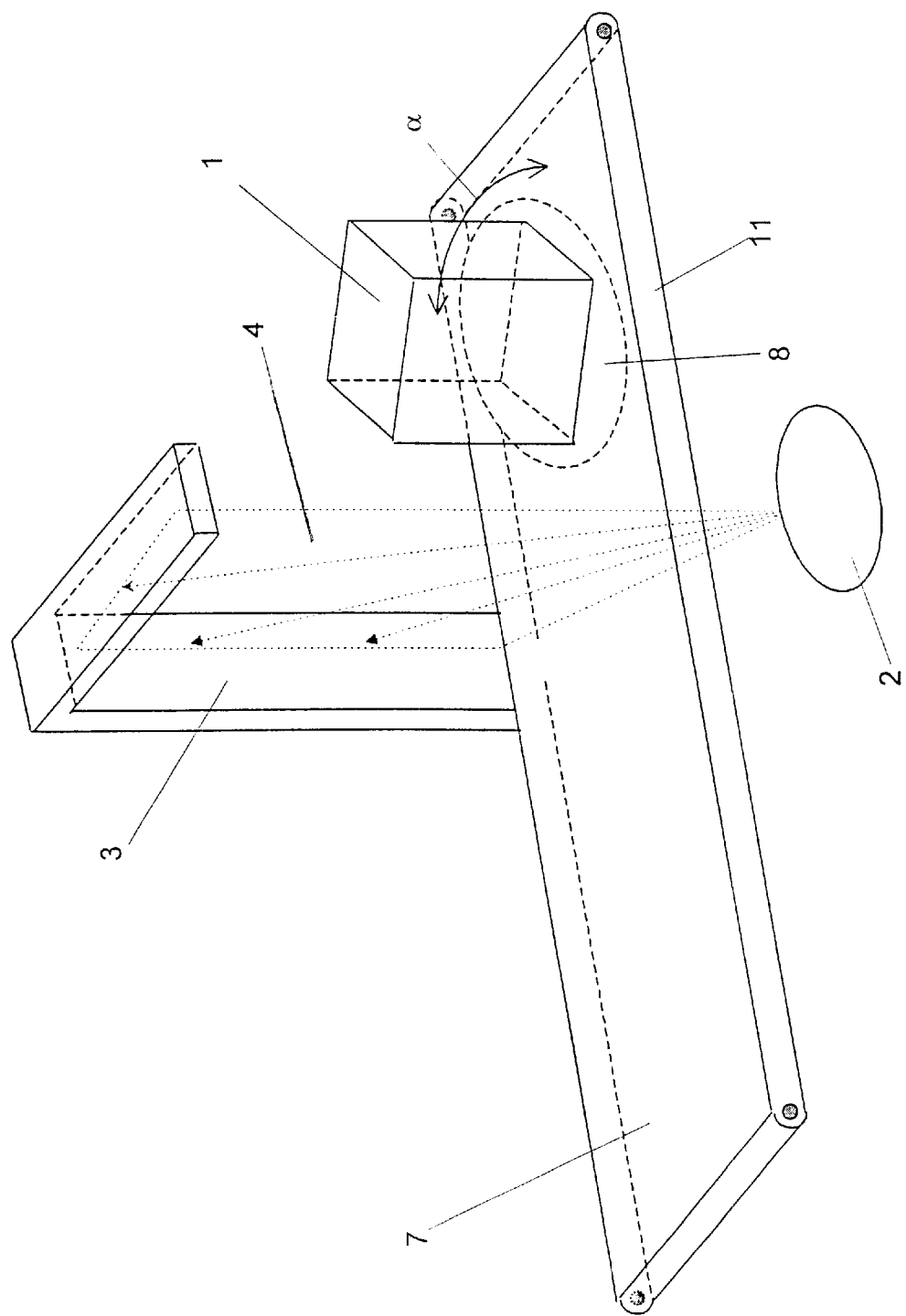
Figure 5:
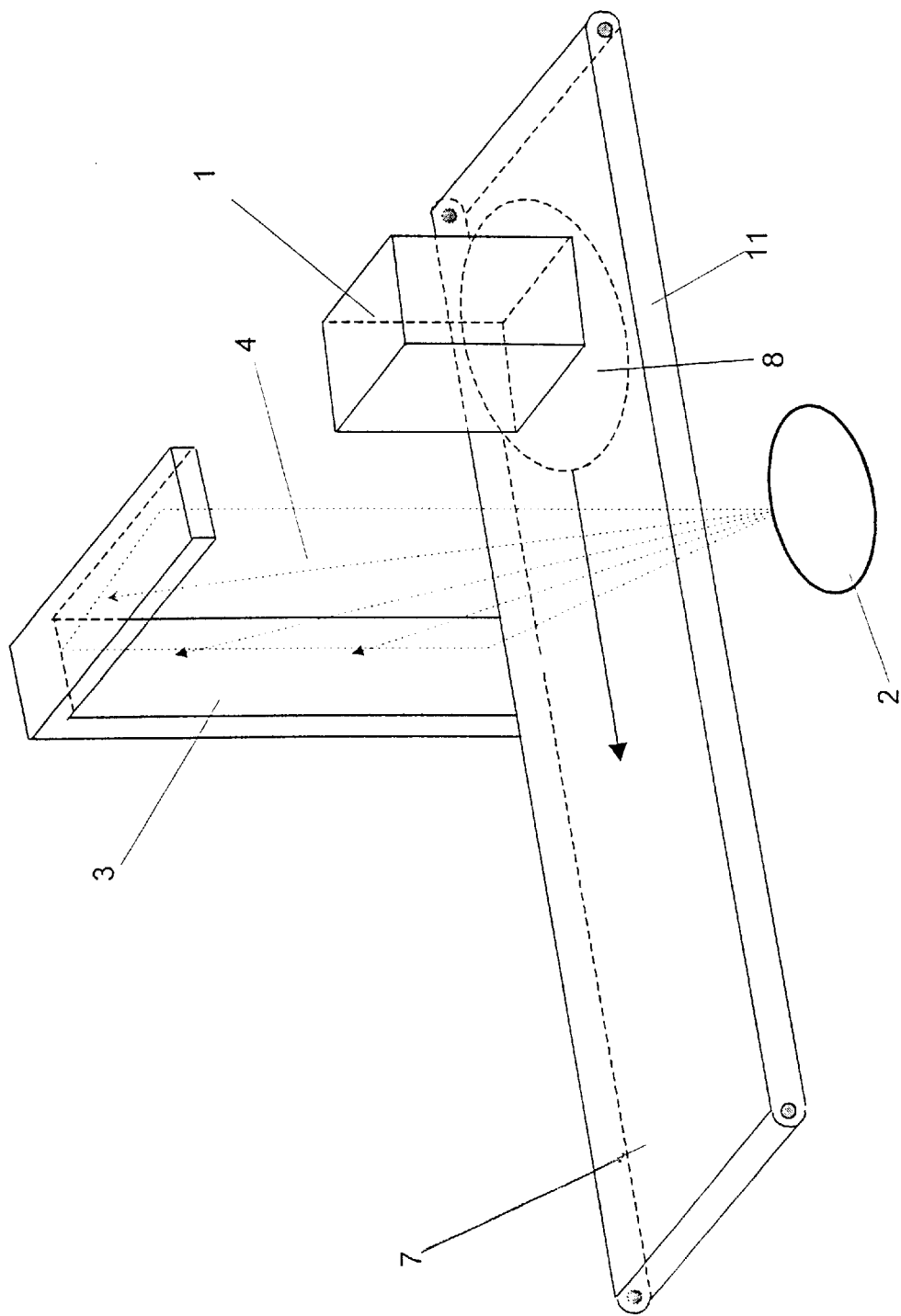

If the image generated on the first pass contains dark areas requiring examination, the object 1, behind the radiation plane 4, is rotated by an angle $\alpha$ into a new transport position (FIG. 4, FIG. 5). In the present embodiment, the object 1 is rotated about an axis that is perpendicular to the transport plane. An operator uses the available image as an aid in making the decision whether the object 1 should be transported through the radiation again and examined, and if so, in what position. The operator manually inputs, via the keyboard 13, the size and/or direction of the angle $\alpha$ through which the object 1 is to be rotated. Then the object 1 is transported back through the radiation plane 4 in the opposite direction, and scanned. The image thus produced is displayed on the screen 6 next to the first image so that the operator can compare the two images. At the same time, the screen 6 displays the angular position of the object and the number of passes it has made through the radiation plane 4.

Figure 6:
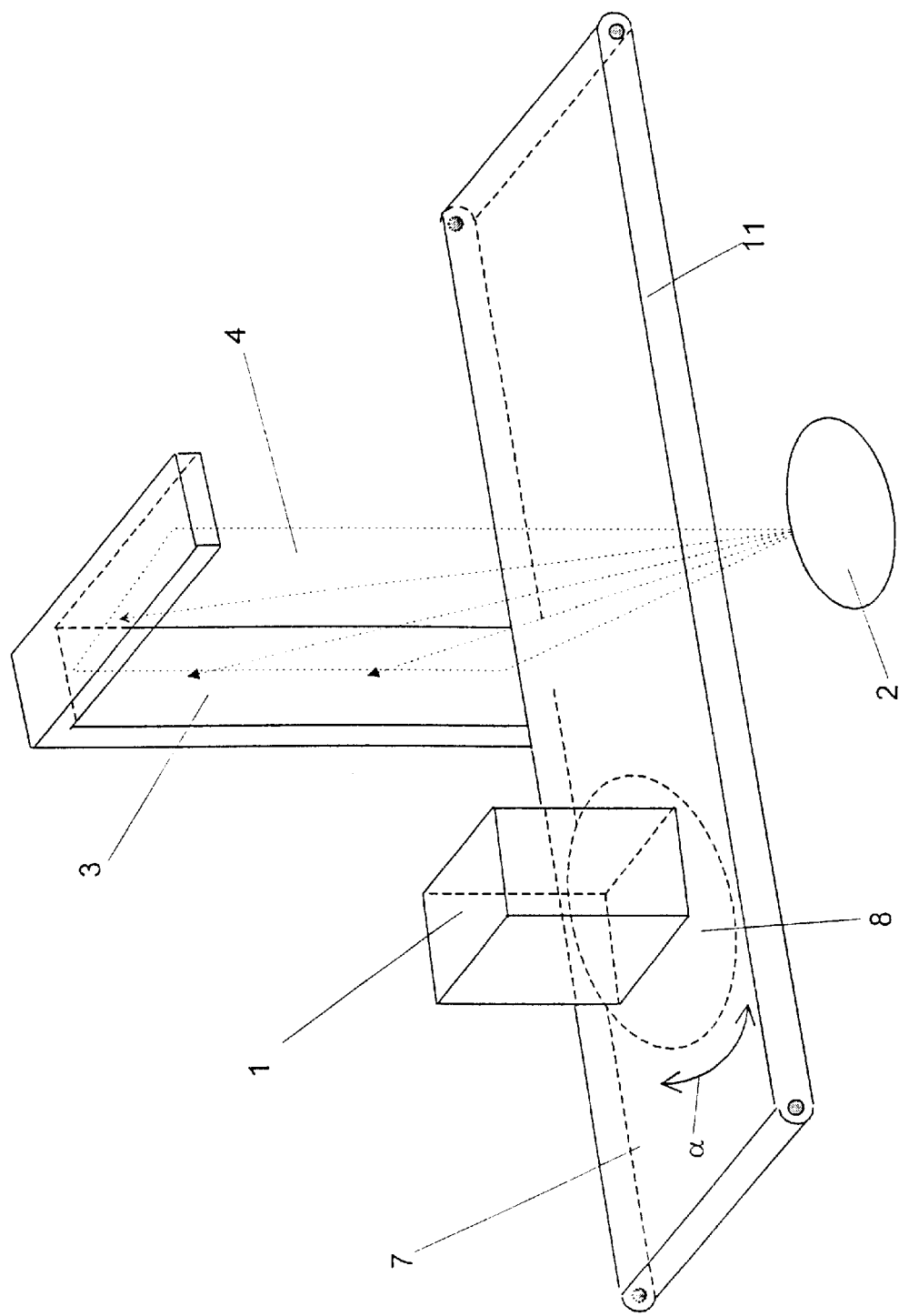
Figure 7:
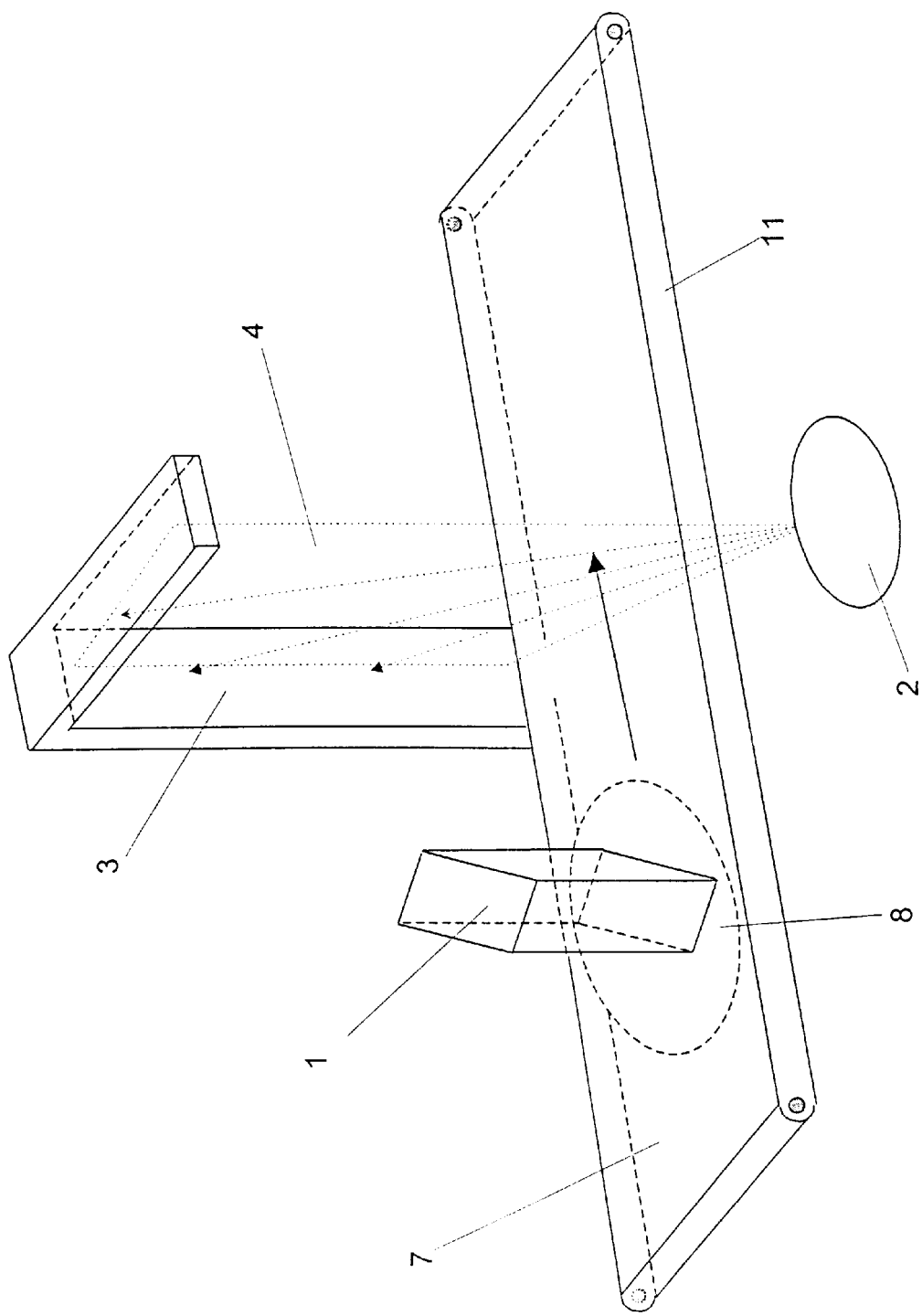
Figure 8:
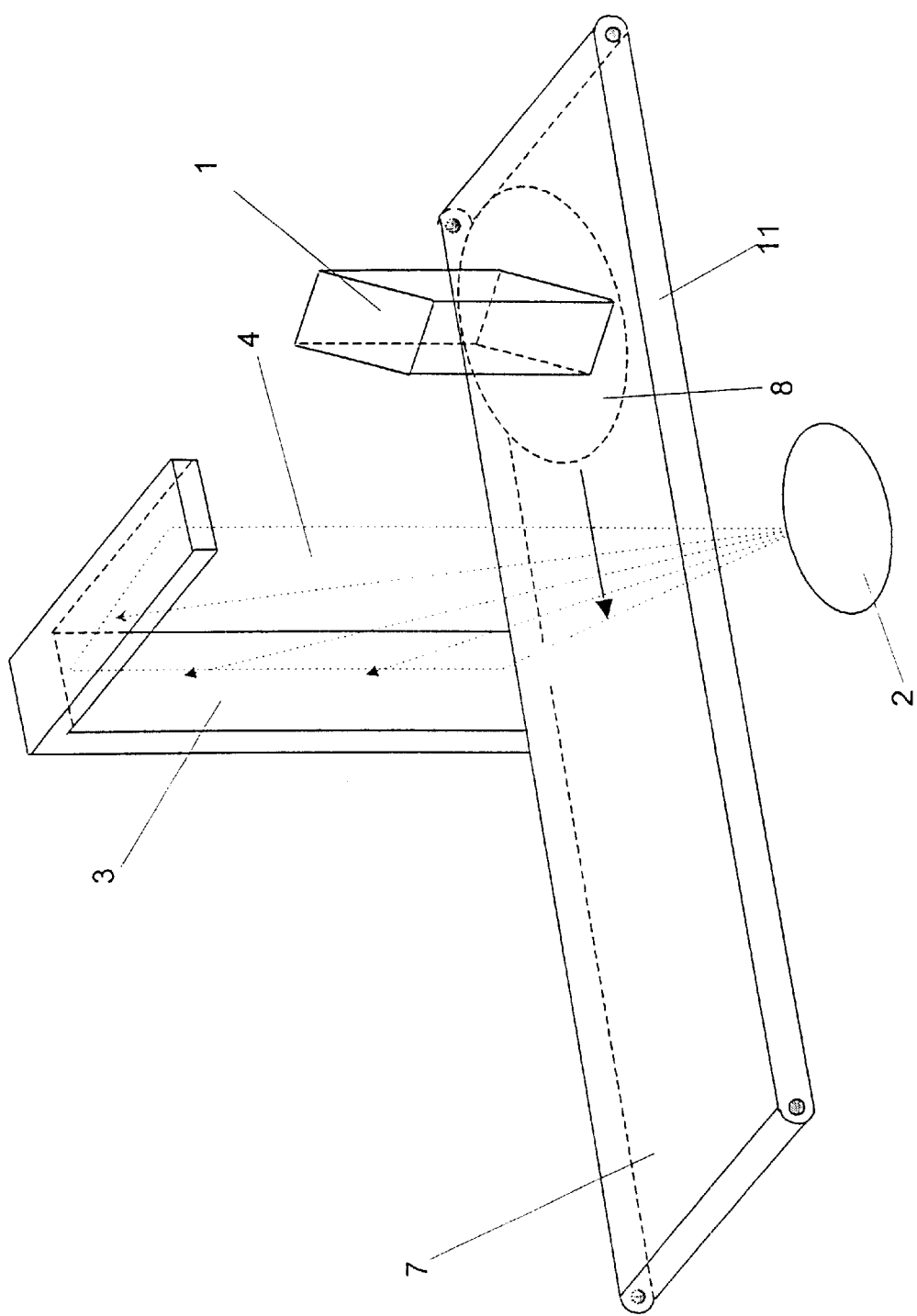
Figure 9:
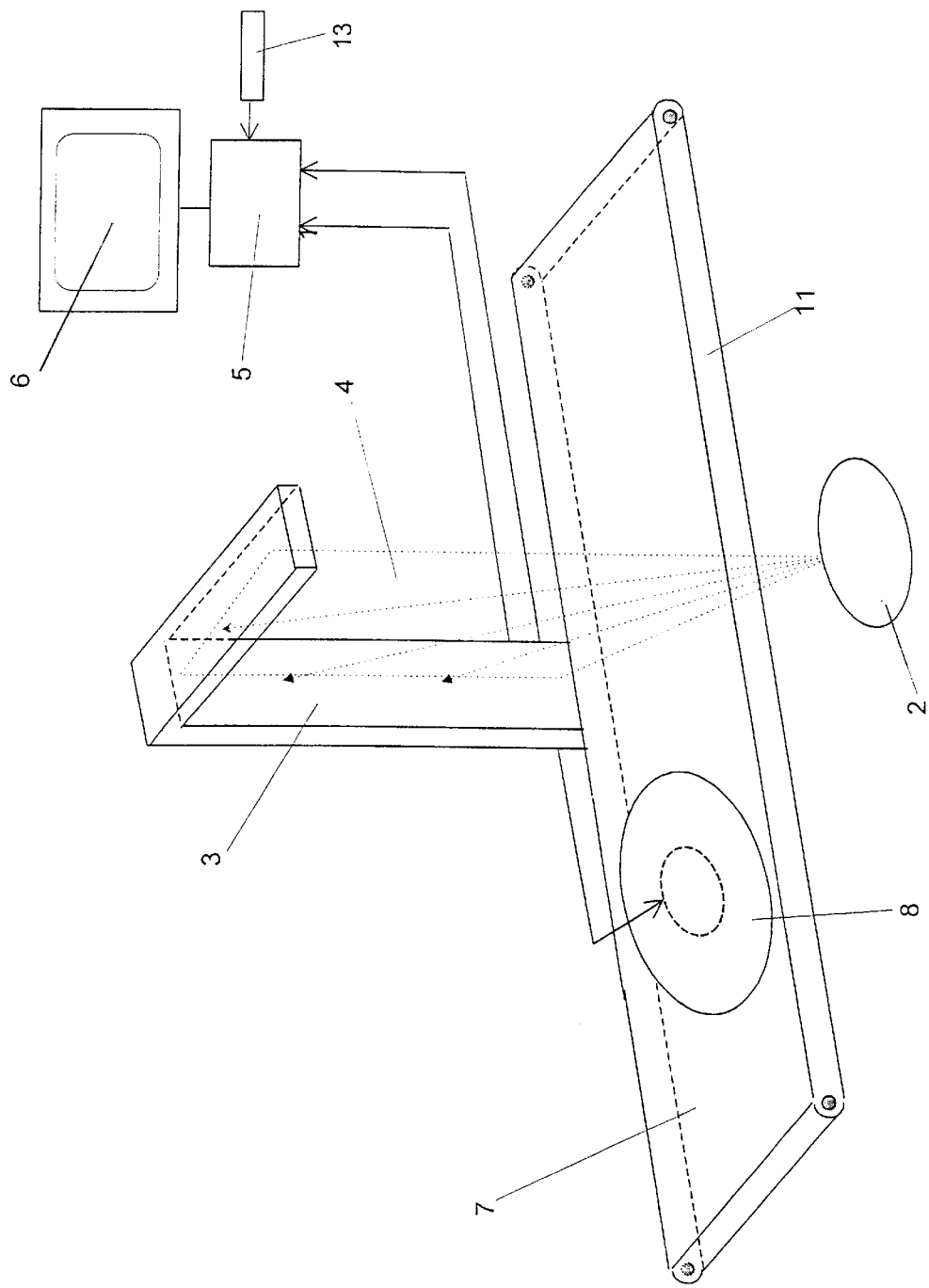
FIG. 9 is an isometric schematic representation of the apparatus of this invention with an associated analysis unit.

The operator uses the generated images to decide after each pass whether the object 1 must again be rotated by a certain angle and rescanned in this new transport position (FIG. 6, FIG. 7). This process is repeated until the items contained in the object 1 are adequately identified with regard to their security relevance. Once this is the case, the object 1 is transported out of the apparatus (FIG. 8).

When the inspection process is automatically controlled, discovery of a dark area triggers an automated inspection routine. In this routine, the computer 5 triggers a number of passes that is either predetermined or determined as a function of the parameters of the dark area. With this method, prior to each pass through the radiation the object 1 is preferably rotated by the same angle, which likewise is either predetermined or determined as a function of parameters from the first image. In this process, the specific angle of rotation and the number of passes are selected such that the individual images of an object 1 can be displayed on the screen 6 in chronological order in similar fashion to a film. To this end, the object 1 is transported through the radiation at least three times. The chronological sequence of the display of the individual images of an object 1 on the screen 6 is chosen so as to create the impression of a rotating object 1. This method of display makes it easier for the operator examining the image to decide whether the object 1 should undergo another inspection stage or be examined manually in addition.

If, as in the case of the embodiment described, images of an object 1 are generated in alternating directions of transport through the radiation, the analysis unit processes the individual images in such a way that they all face the same direction when displayed on the screen 6. Alternatively, it is also possible to generate images only during transport in a single direction. This simplifies analysis of the images during line-by-line detection, since they are all produced in the same direction relative to the radiation and thus can be constructed line-by-line and displayed directly. To this end, either the object 1 is not inspected when it is transported backward in a straight line past the radiation source 2, or the object 1 is transported back for the next pass on a transport loop that leads outside and around the radiation source 2.

We claim:

1. A method for inspecting an object, the method steps comprising:
   emitting radiation by a stationary radiation source;
   transporting the object in a straight line through the radiation;
   detecting the intensity levels of unabsorbed radiation by a detector arrangement;
   processing the detected intensity levels of the unabsorbed radiation into an image of the object; and
   rotating the object through an angle after a pass through the radiation by a rotating device in order to change the object's transport position, and subsequently transporting the object in a straight line through the radiation again, producing another image.

2. The method according to claim 1, wherein the radiation source emits radiation in a radiation plane and wherein the intensity levels of the unabsorbed radiation are detected by the detector arrangement in line-by-line fashion.

3. The method according to claim 1, wherein the object is transported through the radiation in alternating directions of transport, with an image being produced at each pass.

4. The method according to claim 1, wherein the object is transported through the radiation at least three times, with the object being rotated through an angle about the same axis of rotation prior to each pass.

5. The method according to claim 1, wherein the object is rotated through the same angle prior to each pass through the radiation.

6. The method according to claim 1, wherein the object is rotated about an axis of rotation that is perpendicular to a transport plane.

7. The method according to claim 1, wherein the individual images of an object are displayed on a screen in one of the following manners: next to one another and in chronological sequence.

8. The method according to claim 1, wherein an operator manually enters at least one of size and direction of an angle through which the object will be rotated prior to a pass.

9. The method according to claim 3, wherein respective angles of rotation and a chronological sequence of a display of individual images of the object on a screen are chosen such that an impression of a rotating object is produced.

10. The method according to claim 1, wherein the radiation is of X-rays.

11. The method according to claim 1, wherein said step of rotating and subsequently transporting said object through the radiation again is performed, depending upon an input.

12. The method according to claim 11, wherein said input is effected in response to the image of the object that displays the detected intensity levels of the unabsorbed radiation.

13. An apparatus for inspecting an object comprising:
    a stationary radiation source;
    a detector arrangement facing the radiation source;
    a transport device that conveys in a straight line for transporting the object through radiation from the radiation source; and
    an analysis unit with a computer that generates an image from intensity levels detected by the detector arrangement, and a screen that displays the generated image;
    wherein the transport device has a rotating device for rotating the object after a pass through the radiation to change its transport position, and wherein the object is subsequently transported in a straight line through the radiation again.

14. The apparatus according to claim 13, wherein the radiation source emits X-rays.

15. The apparatus according to claim 13, wherein the rotating device has a transport plate that is pivotally mounted to be pivoted by a rotary actuator about an axis of rotation perpendicular to the transport plane.

16. The apparatus according to claim 13, wherein the transport device has a transport plate that is mounted to be tilted by a tilt actuator about a tilt axis running in one of a direction of transport and a direction transverse to the direction of transport.

17. The apparatus according to claim 13, wherein the transport device has a transport plate that is mounted to be at least one of rotated and tilted by an actuator wherein the transport plate with its actuator is carried in a linear guide.

18. The apparatus according to claim 13, wherein is further included a control unit for controlling the transport device and a control-board unit that is connected with the control unit that can used to specify at least one of a number of passes and a size of an angle of rotation.

19. The apparatus according to claim 13, wherein is further included a control unit with a computer that automatically controls at least one of a number of passes and a size of an angle of rotation.

20. The apparatus according to claim 13, wherein is further included a screen and wherein a plurality of images of the object are displayed on the screen in one of the following manners: next to one another and in chronological sequence.

21. The apparatus according to claim 20, wherein the analysis unit processes individual images in such a way that they all face in the same direction when they are displayed on the screen.

22. The apparatus according to claim 20, wherein the analysis unit displays the individual images of an object in their chronological order in such a way that an impression of a rotating object is produced.

23. The apparatus according to claim 13, wherein display instrument is included for displaying to an operator current status parameters of an inspection process.

24. The apparatus according to claim 13, wherein the radiation source emits radiation in a fan-shaped radiation plane, and the detector arrangement contains detectors in linear arrangement.

25. The apparatus according to claim 13, wherein the transport device is reversible for transporting in a first direction and in an opposite direction.

* * * * *